United States Patent [19]

Newman

[11] Patent Number: 4,822,566

[45] Date of Patent: Apr. 18, 1989

[54] OPTIMIZED CAPACITIVE SENSOR FOR CHEMICAL ANALYSIS AND MEASUREMENT

[75] Inventor: Arnold L. Newman, Kensington, Md.

[73] Assignee: The Johns Hopkins University, Baltimore, Md.

[21] Appl. No.: 50,367

[22] Filed: May 18, 1987

Related U.S. Application Data

[63] Continuation-in-part of Ser. No. 799,761, Nov. 19, 1985.

[51] Int. Cl.[4] .......................................... G01N 27/22
[52] U.S. Cl. ................................... 422/68; 324/61 R; 422/69; 422/90; 422/98; 435/817; 436/528; 436/806
[58] Field of Search .................... 422/68, 90, 69, 83, 422/98; 204/403; 324/61 R, 61 C, 60 R, 71.1, 71.4; 436/DIG. 805, DIG. 806, 525, 528; 425/288, 291, 817

[56] References Cited

U.S. PATENT DOCUMENTS

| | | | |
|---|---|---|---|
| 4,072,576 | 2/1978 | Arwin | 436/806 |
| 4,280,815 | 7/1981 | Oberhardt et al. | 436/806 |
| 4,444,892 | 4/1984 | Malmros | 436/151 |
| 4,490,216 | 12/1984 | McConnell | 204/403 |
| 4,562,157 | 12/1985 | Lowe et al. | 436/806 |
| 4,571,543 | 2/1986 | Raymond et al. | 422/98 |

Primary Examiner—Michael S. Marcus
Attorney, Agent, or Firm—Robert E. Archibald; Howard W. Califano

[57] ABSTRACT

An apparatus for detecting the presence and/or measuring the concentration of an analyte in the fluid medium is disclosed. The apparatus relies on biospecific binding between a biochemical binding system and the analyte to change the dielectric properties of a capacitive affinity sensor. The biological affinity sensor is optimized by: (1) adjusting the thickness and dielectric properties of a passivation layer to generally match the impedance of the biological binding system; and (2) minimize the double layer capacitance so that bulk capacitance changes associated with the biological binding system are maximized.

16 Claims, 2 Drawing Sheets

OPTIMIZED CAPACITIVE SENSOR FOR CHEMICAL ANALYSIS AND MEASUREMENT

STATEMENT OF GOVERNMENTAL INTEREST

The Government has rights in this invention pursuant to Contract No. N00024-85-C-5301, awarded by the Department of the Navy.

CROSS-REFERENCE TO RELATED APPLICATION

This is a continuation-in-part of a patent application Ser. No. 799,761, filed on Nov. 19, 1985.

BACKGROUND OF THE INVENTION

1. Field of the Invention

The present invention relates to an apparatus for determining the concentration of an analyte in a fluid medium. More particularly, the invention relates to a capacitive sensor which is uniquely designed to detect a change in the dielectric properties caused by biospecific binding of an analyte with a biochemical binding system. The biochemical binding system is selected to have specific affinity to the particular analyte or group of analytes under test.

2. Description of the Prior Art

Various prior art techniques have attempted to measure the concentration of an analyte in a fluid medium using a binding substance having specific affinity for the analyte. Immunoassays are used to identify analytes, such as haptens, antigens and antibodies in a fluid medium. These immunoassays are based on biospecific binding between components of a reaction pair, such as the biospecific binding between an antigen and an antibody. Tagging one of the components of the binding pair enables more detailed quantification. For example, radioimmunoassay uses a radioisotope as a label for one of the components of the biospecific binding pair. Similarly, fluorescent labels have been used with fluorescent immunoassay.

More recently, attempts have been made to develop an electrochemical sensor which can directly measure analyte concentration. Such sensors would greatly simplify and speed up immunoassay laboratory procedures and provide greater accuracy. These sensors generally detect a change in the physical, electrical or optical properties as one of the binding pairs (generally an antibody) biospecifically binds to its mate pair (generally an antigen). U.S. Pat. No. 4,314,821, issued to Thomas K. Rice detects the change in resonance frequency of a piezoelectric oscillator as antibodies bind to the oscillator. The change in resonant frequency is proportional to the build-up of bound complexes on the oscillator surface (i.e., the build-up of the antibody-antigen complex physically changes the resonance of the oscillator). In U.S. Pat. No. 4,238,757, issued to John F. Schenck, an antigen in a fluid medium is brought into contact with a protein surface layer and alters the charge of the surface layer through an antigen-antibody biospecific binding reaction. A field effect transistor is used to detect this change in charge. Similarly, U.S. Pat. Nos. 4,444,892 and 4,334,880 detects a change in charge which occurs with certain biospecific binding reactions by using a polyacetylene semiconductive device.

U.S. Pat. No. 4,219,335, issued to Richard C. Ebersole, teaches the use of immune reagents labeled with reactance tags. These tags can be detected electrically since they alter the dielectric, conductive or magnetic properties of the test surface. The patent teaches binding a receptor agent to a test surface. The patient's body fluid containing a certain antibody is added to the test area and the antibody complexes with the receptor agents. In a second step, the test area is exposed to a second immune reagent that is bonded to a reactance tag. This immune tag complexes with the receptor agent-patient antibody complex, if present, on the test surface. The reactance tag containing a metal or metal-oxide is then detected by electrical means.

U.S. Pat. No. 4,054,646, issued to Ivar Giaever, teaches a method for determining, by electrical means, whether an antigen-antibody reaction produces a monomolecular layer or a bimolecular layer. An antigen is used to coat a metal substrate. The coated substrate is then brought into contact with the fluid suspected to contain a certain antibody. If the antibody is present it adheres to the antigen layer forming a bimolecular layer. If the antibody is not present, a monomolecular layer remains. The next step is to place a mercury drop on the upper layer and measure the capacitance between the mercury drop and the metal substrate. Since the distance between the mercury drop and the metal substrate changes for the bimolecular layer as compared to the monomolecular layer, the measured capacitance also changes. U.S. Pat. No. 4,072,576, issued to Hans Arwin et al, teaches measuring the alternating voltage impedance between two platinum electrode plates immersed in a fluid medium. A biochemical substance, is adsorbed onto the metallic surface. If the fluid under test contains an analyte biospecific to the adsorbed substance binding will occur. For example, an antigen may be absorbed directly on the metal electrodes and a specific antibody in the test fluid may bind to it forming a complex which remains on the surface of the metal electrodes. The capacitance changes depending on whether the surface is coated with a monolayer of the antigen or whether a bimolecular layer, composed of antigen and antibody layers, are adsorbed onto the surface.

SUMMARY OF THE INVENTION

The present invention represents a new type of electrochemical sensor for determining the concentration of an analyte in a fluid medium. The invention has increased speed and accuracy compared to prior art methods.

U.S. patent application entitled "Capacitive Sensor for Chemical Analysis and Measurement", Ser. No. 799,761, filed Nov. 19, 1985, which is incorporated herein by reference, describes the following features of the present invention:

a. The invention utilizes an "open" capacitor which produces a higher electric field in a volumetric region adjacent to the biological binding layer. The electrodes of the "open" capacitor are coated with an insulating passivation layer. The biological binding layer is immobilized on the insulating passivation layer by linking molecules. Biospecific binding reactions are used to draw into or release biochemical molecules from the binding layer. Movement of these biological molecules displaces molecules of the fluid medium which has a different dielectric constant, thereby causing a change in the capacitance of the sensor.

b. The sensor has two general embodiments. In the first embodiment, referred to as the direct binding configuration, binding agent molecules are immobilized to the passivation surface with linking molecules. The binding agent molecules may be antibodies or antigens. The binding agent molecules are biospecific with a particular analyte, such as a virus, bacteria, antibody, or large molecule. As fluid containing the analyte is introduced onto the sensor, the analyte binds to the immobilized binding agent. As the analyte binds to the immobilized binding agent, the dielectric properties of the "open" capacitor are modified.

The second embodiment, referred to as the competitive binding embodiment, uses a more elaborate biochemical binding system. This method is preferred when the analyte molecules are relatively small. The biochemical binding system has a first layer of the analyte or analyte-analog immobilized to a surface with linking molecules. A second layer of a binding agent, biospecific to the analyte, is bound onto the immobilized analyte layer. The binding agent molecules are larger molecules and have a lower dielectric constant than the fluid medium. When free analyte molecules in the fluid medium are introduced onto the sensor, they compete with the immobilized analyte molecules to bind with the binding agent molecules. This competitive binding results in a certain amount of the binding agent molecules forming a complex with the free analyte molecules. The free analyte-binding agent complex then diffuses from the surface changing the measured capacitance.

c. The invention also teaches combining the invented analyte affinity capacitor with at least one reference capacitor to form a differential affinity sensor. The reference capacitor is used to compensate for nonanalyte effects. These non-analyte effects include changes in the dielectric constant of the fluid medium caused by a change in temperature, ionic concentration, pH, composition and physical state of the fluid medium, as well as non-specific binding of other proteins contained within the fluid medium.

d. The invented capacitive sensor can be used to measure the concentration of specific analytes in body fluids and can function as either an in vivo or in vitro sensor. The capacitor sensor can also be used to detect specific substances in the environment. The use of the reference capacitor allows the sensor to continuously measure analyte concentration even though the physical and chemical characteristics of the fluid medium containing the analyte may change. The capacitance affinity sensor can be used to detect a broad range of analytes including: bacteria, viruses, antibodies, large protein molecules, antigens, haptens, polysaccharides, glycoproteins, glycolipids, enzyme inhibitors, enzyme substrates, neurotransmitters and hormones.

The present specification discusses optimization of the invented capacitive affinity sensor by: (1) adjusting the thickness and dielectric properties of the insulating passivation layer so that the capacitance of the passivation layer approaches the biological binding layer capacitance; (2) minimizing the undesirable effect of the double layer phenomena common when an electrolyte is present in the fluid under test, so that the desired bulk dielectric changes associated with the biological binding layer are maximized.

DETAILED DESCRIPTION OF THE PREFERRED EMBODIMENTS

The Capacitive Chemical Sensor can be made chemically sensitive to an analyte by any of a variety of biospecific chemical binding methods. These biospecific binding methods fall into two general categories: (1) competitive binding configuration, and (2) direct binding configuration. As used herein, the term "analyte" means the species to be analyzed.

Direct Binding Embodiment

Figure 1A:
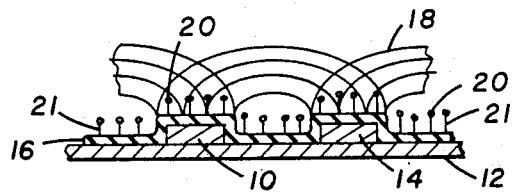
FIGS. 1a and b are schematic cross-sectional views of the direct binding configuration with FIG. 1a showing the structure of the capacitive sensor, and FIG. 1b illustrating the operation of the capacitive sensor to detect the presence of an analyte in a fluid medium.

FIG. 1a is a schematic cross-sectional view showing the first general configuration of the sensor, referred to as the direct binding configuration. A first conductor 10 is positioned on the surface of an insulating material or substrate 12; and, a second conductor 14 is also positioned on substrate 12 and disposed a distance from the first conductor 10. The two conductors 10, 14 are coated with a thin electrically insulating passivation layer 16, and the resulting structure forms an "open" capacitor. When a direct alternating voltage is applied across the conductors, an electric field is generated having electric lines of flux 18. As seen generally in FIG. 1a, the electric field has a higher field intensity within the volumetric region adjacent to the "open" face capacitor.

Molecules of a binding agent 20 are immobilized the passivation layer 16 with linking molecules 21. In FIG. 1a, the layer of the immobilized binding agent coats the entire passivation surface 16. The binding agent is an affinity ligand that will bind specifically to the analyte, such as an antibody binds specifically to a particular virus or as an antigen binds specifically to a particular antibody. Alternatively, the affinity ligand may bind to a specific group of analytes, such as nucleotide analogs and lectins bind to certain groups of biochemical analytes.

Figure 1B:
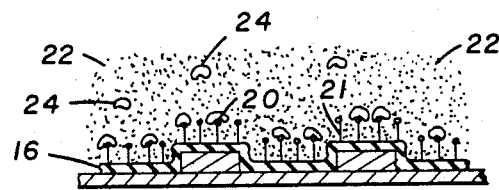

In FIG. 1b, a fluid medium to be tested for a particular analyte is introduced onto the "open" capacitor. The sensor may be immersed into the fluid as in the case of an in vivo medical sensor or an environmental sensor; or, a small volume of the fluid medium may be poured onto the sensor. The fluid medium, shown in FIG. 1b, is composed of molecules of fluid 22 and molecules of analyte 24. The fluid medium may be body fluids such as blood, urine, tears, saliva, semen or it may be other buffered solutions containing the analyte. The fluid molecules 22 will generally include water molecules and small amounts of protein molecules, ionic substances, etc.

In operation, when an analyte species in the fluid medium enters the "open" capacitor sensor and approaches the surface, it binds to the immobilized binding agent (i.e., the ligand layer). The linking molecule 21 and binding agent 20 structure provides a concentrating function, concentrating analyte on to the biological binding layer. The linking molecule must bind the binding agent with sufficiently strong binding chemistry so it will not be pulled off from the passivation surface 16 during the binding reaction (usually covalent bonding is used). This binding will occur until equilibrium is reached between the binding agent, the analyte, and the binding agent-analyte complex (i.e. the ligand-analyte bound species). This equilibrium relationship can be related by the following equation:

$$(A) + (B) \rightleftharpoons (A \cdot B),$$

where
A = Analyte,
B = Binding Agent and
(A·C) is the Bound Complex.

As the analyte species binds to the biological binding layer, fluid molecules are displaced and the resulting dielectric constant associated with the biological binding layer will decrease. This change in the dielectric constant will be proportional to the analyte species concentration as related by the following equations:

$$\frac{[A \cdot B]}{[A][B]} = K \qquad (1)$$

$$T_A = [A] + [A \cdot B] \qquad (2)$$

$$T_B = [B] + [A \cdot B] \qquad (3)$$

where,
[A] = free analyte concentration
[B] = binding agent (ligand) concentration
[A·B] = bound analyte-ligand complex
$T_A$ = total analyte concentration
TB = total binding agent (ligand) concentration It is to be understood that the above equilibrium equations are only approximations and are used only to illustrate the general functioning of the sensor. The quantity $T_B$, the number of immobilized binding agent molecules, is known; the quantity K is known or can be determined by experimentation; the concentration [A·B] is measured by the change in the dielectric constant of the "open" capacitor; and, the total concentration of the analyte in the test fluid ($T_A$) is what one wants to determine.

Usually, but not exclusively, the analyte species for the direct binding configuration will be large molecules (generally larger than 150,000 daltons) such as bacteria, viruses, antibodies, or protein molecules. The larger the analyte molecule and the lower its dielectric properties, the greater will be the change in the capacitance of the sensor as the analyte binds to the biological binding layer. It will be noted that when the analyte is bound to the binding agent, its mobility in the electric field is decrased and correspondingly its dielectric constant is lowered. When dielectric constant of the bound analyte is lower than the fluid (generally water) that it displaced from the vicinity of the biological binding layer, the capacitance of the sensor will be modified. Table I contains a non-limiting example of the type of binding agents (ligands) and analytes that can be used with the direct binding configuration of the sensor:

TABLE I

| immobilized binding agent | analyte |
|---|---|
| bio-specific antibody | bacteria |
| bio-specific antibody | viruses |
| bio-specific antibody | a second antibody |
| bio-specific antibody | large molecule analytes such as protein molecules |
| bio-specific antigen | antibody |
| bio-specific hapten | antibody |
| bio-receptor | hormones, neural transmitters, toxins |

Competitive Binding Embodiment

Figure 2A:
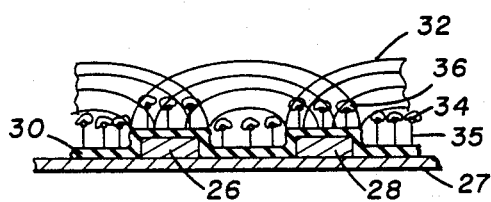
FIGS. 2a and 2b are schematic cross-sectional views of the competitive binding configuration with FIG. 2a showing the structure of the capacitive sensor and FIG. 2b illustrating the operation of the capacitive sensor to detect the presence of an analyte of in a fluid medium.

The second general embodiment of the present invention is shown in the schematic cross-sectional view of FIG. 2a. This embodiment is referred to as the competitive binding configuration of the sensor and is useful in sensing analytes that are "small" molecules. In this case, small is defined as significantly smaller in molecular weight than 150,000 daltons (1 dalton =1 atomic mass unit). A first conductor 26 is positioned on the surface of an insulating material or substrate 27; and, a second conductor 28 also positioned on substrate 27 is disposed a distance from first conductor 26. The two conductors 26, 28 are coated with a thin electrically insulating passivation layer 30, and the resulting structure forms an "open" capacitor, similar to that used in the first direct binding embodiment. As with the first embodiment, when a direct or alternating voltage is applied across the conductors, an electric field is generated having electric lines of flux 32.

The essential difference between the direct and competitive binding embodiments is that a two-layer biochemical binding system is used in the latter. A first layer 34 is made from molecules of the analyte or an analog of the analyte that is immobilized to the passivation 30 surface by linking molecules 35. A second layer 36 is made from molecules of a binding agent that are biospecific with the analyte. The second layer 36 binds to the immobilized analyte layer 34. The molecules of the binding agent are generally large compared to the analyte molecules.

Figure 2B:
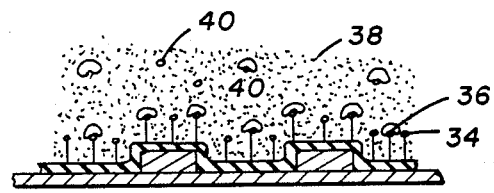

In FIG. 2b, the fluid medium to be tested for a particular analyte is introduced onto the "open" capacitor, as was done with the direct binding embodiment. The fluid medium that can comprise body fluids or a fluid buffer, is composed of fluid molecules 38 and analyte molecules 40. The fluid molecules 38 will generally include water molecules, as well as small amounts of protein molecules, ionic substances, etc. The binding agent is selected to have a dielectric constant lower than the dielectric constant of the dominant fluid molecule, generally the water molecule; and, the binding agent molecule is selected to be substantially larger than the dominant fluid molecule.

In operation, when analyte species in the fluid medium enters the "open" capacitor sensor and approaches the two-layer biochemical binding system, it competes with the immobilized analyte 34 to bind with binding agent molecules 36. Since the binding agent molecules are in dynamic equilibrium, there is always a small fraction of these molecules not bound to the immobilized analyte. When free analyte enters into the system, some of these unbound binding agent molecules bind to the free analyte. This results in an overall loss of the binding agent molecules from the surface of the biochemical binding system as equilibrium is restored. The binding agent-free analyte complex diffuses from the binding system, allowing higher dielectric fluid molecules to enter the biological binding layer. The result is an increase in the dielectric constant of the capacitor. This change in the dielectric constant will be proportional to the concentration of the analyte species as related by the following equations:

$$\frac{[A \cdot C]}{[A][C]} = K1 \tag{4}$$

$$\frac{[A \cdot B]}{[A][B]} = K2 \tag{5}$$

$$T_A = [A] + [A \cdot C] + [A \cdot B] \tag{6}$$

$$T_B = [B] + [A \cdot B] \tag{7}$$

$$T_c = [C] + [A \cdot C] \tag{8}$$

where
[A] = binding agent concentration
[B] = free analyte concentration
[C] = immobilized analyte concentration
[A·B] = free analyte-binding agent complex
[A·C] = immobilized analyte-binding agent complex
$T_A$ = total binding agent concentration
$T_B$ = total free analyte concentration
$T_c$ = total immobilized analyte concentration It is again to be understood that the above equilibrium equations are only approximations and used only to illustrate the general functioning of the sensor. For these equations, the quantity $T_A$, the number of binding agent molecules, is known; the quantities $K_1$ and $K_2$ are known or can be determined by experimentation; the concentration [A·C] is measured by the change in the dielectric constant of the "open" capacitor; the quantity $T_c$, the number of immobilized analyte molecules, is known; and, the total concentration of the analyte in the test fluid ($T_A$) is what one wants to determine.

The binding agent that forms the second layer of the biochemical binding system can be selected from general or specific affinity ligands and may include, but is not limited to, antibodies, lectins, enzymes and receptors. The immobilized analyte which forms the first layer of the biochemical binding system may be the same molecular substance as the analyte under test, or it may be an analog of the analyte that is biospecific to the binding agent. The immobilized analyte may, for example, be an antigen, a hapten, a polysaccharide, a glycoprotein, a glycolipid, an enzyme inhibitor, an enzyme substrate, a neurotransmitter, a hormone, etc. Table II contains nonlimiting examples of the biochemical binding system used in a competitive binding embodiment to test for particular analytes.

TABLE II

| biochemical binding system | | | class of |
|---|---|---|---|
| immobilized analyte | binding agent | analyte | sensor |
| antigen | antibody | antigen | A |
| hapten | antibody | hapten | A |
| polysaccharides | lectin | polysaccharides | B |
| glycoproteins | lectin | glycoproteins | B |
| glycolipids | lectin | glycolipids | B |
| enzyme inhibitor | enzyme | enzyme inhibitor | C |
| enzyme substrate | enzyme | enzyme substrate | C |
| enzyme inhibitor | enzyme | enzyme substrate | C |
| neurotransmitters | neural receptor | neurotransmitters | D |
| hormones | neural receptor | hormones | D |

As can be seen from Table II, there are four classes of the competitive binding sensor. In class A the binding agent is an antibody specific to the analyte. The analyte may be an antigen or hapten. The biochemical binding system comprises a first immobilized layer of the antigen or hapten analyte with a second layer of the biospecific antibody biochemically bound to the immobilized analyte in the first layer.

In class B, the binding agent is a lectin, which is a general ligand specific to a group of analytes. A lectin-based sensor can be made more specific by an appropriate molecular sieve membrane that excludes larger molecules in the general analyte group from reacting with the biochemical binding system. In this class, for example, the binding system could have a first immobilized layer of a polysaccharide or a membrane protein containing sugar residues of certain configurations and a second layer of the general lectin bound to the first layer.

In class C, the binding agent is an enzyme reactive with an enzyme inhibitor or enzyme substrate. In this class, for example, the binding system could have an inhibitor for a particular enzyme immobilized on the sensor surface and a second layer containing the enzyme bound to the inhibitor in the first layer. With a particular enzyme substrate in the test fluid, the enzyme binding agent will be drawn from the surface of the binding system.

In class D, the binding agents are neuroreceptors. The neuroreceptor has its function greatly altered by various neurotoxins and other agents. The binding system can have a layer of succinylcholine immobilized on the sensor surface with a second layer of acetylcholine receptor molecules bound to the first layer. If a neurotoxin, for example, is present in the test fluid, the receptor binding behavior will be altered and it will be released from the binding system surface, thereby altering the dielectric properties of the sensor. It is of course to be understood that these are merely examples of the biochemical binding systems that can be used with the competitive binding embodiment of the present invention.

"Open" Capacitor Structure

Figure 3:
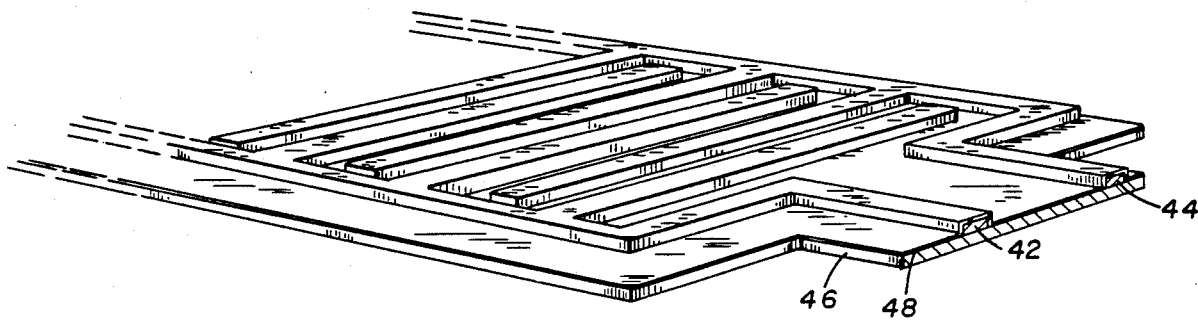
FIG. 3 is a perspective view of an "open" capacitor that uses a plurality of interdigitate fingers.

FIG. 3 is a perspective view of an "open" capacitor that uses a plurality of interdigitated fingers. Metallic conductors 42 and 44 are positioned on an insulating substrate 46. Each conductor has a plurality of fingers that are disposed in an interdigitated manner relative to the fingers of the other conductors. Known photolithographic etching techniques are used to form the interdigitated fingers on the substrate. The substrate can be made from insulating materials such as Corning 7059 glass or alumina wafers. The interdigitated fingers can be made of copper and gold, although both conducting or semiconducting material may be used. Applicant selected 2 mil wide fingers that are approximately 0.5 mil high and separated by 3 mil spaces, although other dimensions may be used. (In fact, the electrode fingers may be imbedded in the substrate rather than being deposited on the structure.) The interdigitated fingers are covered with an insulating passivation layer 48. Applicant has made the insulating layer 48 with a 1-2.5 micron coating of parylene polymer deposited using known deposition processes and a 0.3 micron of SiO deposited using vapor vacuum evaporation deposition; however, alternative electrically insulating passivation material can be used.

Optimization of passivation layer

An important element in the design of the capacitive affinity sensor is the choice of material and thickness for the passivation layer (element 48, FIG. 3). The passivation layer serves two functions. The first is that it must prevent the movement of water or ions to the surface of the metallic electrode where electrolysis reactions may cause changes in the electrode surface (i.e., corrosion) that would result in a significant drift in the baseline. The second function is that the passivation layer provides a reactive surface that allows chemical linking of the haptens or other binding molecules to the surface of the sensor with linking molecules.

However, the passivation layer can serve another function. To understand this it is necessary to look at the way the capacitances of different layers interact. The capacitances of the passivation layer and the biological layer can be looked upon as two capacitors in series. Series capacitances are combined using the relationship:

$$C = \frac{1}{1/c_1 + 1/c_2}$$

Figure 4:
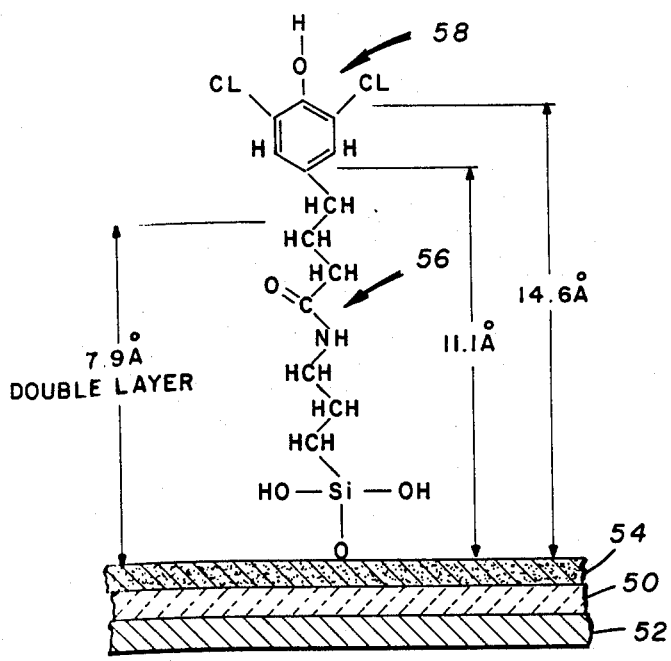
FIG. 4 is a drawing of antigen binding agent bound to a passivation layer by linking molecules.

The consequences of this formula are that small capacitances have a greater effect than large capacitances in determining the overall measurable capacitance of the two layers. In the capacitive affinity sensor the desired capacitance modulation occurs in the biological binding layer. Therefore, in order to see the greatest change in the overall capacitance, it is important to have the passivation layer capacitance be as close as possible to the biological binding layer capacitance. There are two parameters that can be manipulated to help to match the capacitances. These are the thickness of the passivation layer and its dielectric constant. In order to raise the capacitance of the passivation layer it should be as thin as possible in keeping with its passivating function. The choice of materials will dictate the dielectric constant. However, this must be balanced against both the passivation function and ease of binding the biological chemistry to the surface. One solution to the latter problem is the use of two layered passivation as shown in FIG. 4. The bottom layer 50 is deposited on electrode 52 and provides the real protection against water and ions and a second thin outer layer 54 provides the binding capability. An example of this is the use of silicon nitride as a passivating material. Silicon nitride has very good resistance to water and ions allowing it to be used in films of 3000 Å or less. In addition, its relatively high dielectric constant (6 to 8) further helps to raise the capacitance of the passivating layer. To this may be attached a layer of a poorer passivation material such as silica which is more reactive with a silane linking molecule In summary, the passivation layer is optimized in the following ways:

A. A very dense, water and ion impervious thin film material is chosen such as Silicon Nitride, although there are others that would work almost as well.
B. The thickness of the film is kept within an order of magnitude of the thickness of the biological layer. The thickness is technologically limited by the ability to produce a thin film that has no pin holes. The thinner the film, the better the chance of it having pinholes. A film thickness of from 500 to 3000 Å is reasonable.
C. The dielectric constant of the film should be as high as possible and match closely with the dielectric constant of the biological binding layer.
D. The passivation layer must provide a good binding site for the linking molecules. When a silane linking molecule is used, a thin silica (silicon dioxide) layer covering the passivation layer may be desirable.

Optimization of Linking Molecule Structure

The biological binding layer for either the direct or competitive systems is bound to the passivation layer by linking molecules. The linking molecules perform the following functions:

A. The biological binding layer (the antigen, for example, in the direct configuration) must be held out from the surface far enough to be presented immunologically with no steric hindrance between the analyte and the surface.
B. The biological binding layer must be chemically bound to insure that it is stable, that is, that it does not come off the surface. If it were merely adsorbed onto the surface, there would be a finite desorption. The linker molecule confers generality to the system because any molecule could be chemically bound to a surface without having to rely solely on its non-specific adsorption properties (some molecules adsorb strongly to certain surfaces and some molecules adsorb hardly at all).
C. The linking molecule should be long enough to insure that the antigen or other immobilized chemical is held far enough from the surface so as to avoid interference with any binding process that might be necessary for the proper function of the sensor. Note that the linking molecule length keeps the chemistry outside the normal dimensions of the undesirable double layer capacitance.
D. The linking molecule serves to physically and chemically stabilize the biological component of the sensor and this helps prevent its degradation over time.

The Capacitive Affinity Sensor works through the modification of the bulk solution capacitance, and not through a disruption of the double layer formed around an electrode when a potential is applied. To illustrate this, we will present as an example a sensor capable of binding antibodies to pentachlorophenol (see FIG. 4). The sensor s passivated with a 2000 Å coating of silicon nitride 50 and a thin layer of silica 54. The passivation layer is then covered with 3-aminopropyltriethoxysilane. The amino group is then linked to a pentachlorophenol analog, 2,6-dichlorophenol through a butanoic acid linker molecule 56. The solvent system is phosphate buffered saline (0.01 M phosphate, 0.9% NaCl, pH 7.4).

A major factor preventing this sensor from reacting to changes in the double layer is that the active element of the hapten coating, the 2,6-dichlorophenol group 58 as well as the antibodies are outside of the double layer.

The antibodies responsible for the capacitive change in the sensor bind to the dichlorophenol group 58. Molecular mechanics calculations of the geometry of the molecules attached to the surface show that the distance between the linking oxygen atom attached to the silane and the closest carbon of the benzene ring is 11.1 Å. The distance to the phenolic oxygen is 14.6 Å. The antibody extends out an additional 100 Å. The size of the double layer only extends out 7.9 Å. Thus, the active part of the capacitive affinity sensor is substantially outside of the double layer.

Minimization of Electrical Double Layer Effect

In addition to the capacitance of the passivation layer and the biological binding layer an additional capacitance is present if there are electrolytes in the test solution. This additional capacitance is due to the capacitance of the "electrical double layer". However, in the capacitance affinity sensor, as discussed above, this capacitance is insignificant with regard to the passivation layer and biological layer capacitance, because of the large value of the double layer capacitance. As noted, above in combining capacitances in series, the capacitor with the smallest capacitance has the dominant influence. Data in the literature (D.C. Graham "Chemical Reviews", Vol. 41, pg. 441, 1947) shows that the double layer capacitance is on the order of 10s of microfarads per cm$^2$ ($\mu f/cm^2$) compared to less than 1 $\mu f/cm^2$ for the biological layer and less than 0.03 $\mu f/cm^2$ for the passivation layer (2000 Å silicon nitride). As a result, the double layer capacitance, or any modification to it by direct adsorption of a molecule onto the passivation layer will not be sensed by the system. The capacitance provided by the passivation layer is a major factor in eliminating the effect of the double layer capacitance. The length of the linking molecule (as shown in FIG. 4) also extends the biological binding layer out beyond the double layer effect. These factors reduce the effect of the double layer capacitance and permit the "open" face capacitance to sense the bulk dielectric changes in the biological binding layer. The present invention does not rely on the double layer capacitance because it is unreliable. Specifically, double layer capacitance measurements requires the use of very clean conducting electrodes. Non-specific adsorption of substances such as dirt, or oxidation of these conductors will cause variations in the measured capacitance of the double layer. For this reason the present invention relies on bulk capacitance measurements of the biological binding layer instead of double layer measurements. As discussed earlier, this bulk dielectric change in the biological layer is due to the displacement of higher dielectric fluid molecules (primarily water) by biological molecules binding to the biological binding layer.

Differential Capacitive Sensor

Figure 5A:
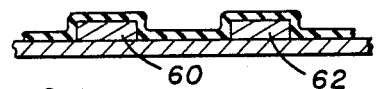
FIGS. 5a, b and c are schematic cross-sectional views showing various embodiments of the reference capacitor with FIG. 5a showing a reference capacitor which does not contain the biochemical binding system, FIG. 5b showing a reference capacitor that uses a "dummy" binding agent for the binding system, and FIG. 5c showing a reference capacitor using a binding system composed of a "dummy" analyte and binding agent pair.
Figure 5B:
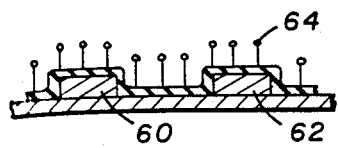
Figure 5C:
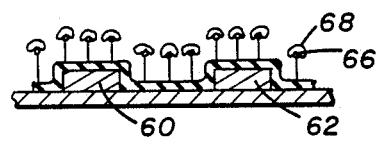

The accuracy of both the direct binding and competitive binding embodiments of the present invention is increased if differential sensing is employed. The differential capacitive sensor uses an analyte affinity sensor (i.e., the direct binding capacitive sensor or the competitive binding capacitive sensor discussed above) and at least one reference capacitor to compensate for non-analyte effects. The reference capacitor compensates for changes in dielectric constant of the fluid medium caused by changes in temperature, ionic concentration, pH, composition and physical and chemical state of the fluid medium, as well as non-specific binding of proteins that may be in the fluid medium. FIGS. 5a, b, and c, show various embodiments of the reference capacitor. Each reference capacitor has a first and second conductor 60, 62 positioned on a substrate to form the "open" capacitor as described above. In FIG. 5a, a reference capacitor that can be used with both the direct and competitive binding embodiments is shown. This reference capacitor has no protein coat, i.e., it does not have the immobilized binding agent or binding system. In FIG. 5b, a reference capacitor for use with the direct binding embodiment is shown. This reference capacitor contains an immobilized layer of a "dummy" binding agent 64. The "dummy" binding agent is selected from the same class as the analyte sensitive binding agent but it is made biospecific to a molecule not found in the test environment. Alternatively, if the reference capacitor uses the same binding agent as the affinity capacitor, a molecular sieve would be used to prevent the analyte from entering the reference capacitor. In FIG. 5c, a reference capacitor for use with the competitive binding embodiment is shown. This reference capacitor contains a "dummy" biochemical binding system. The "dummy" binding system uses an immobilized "dummy" analyte 66 specifically reactive with a "dummy" binding agent 68. The "dummy" analyte and binding agent are chosen to have an affinity constant and other physical characteristics that closely match the real analyte and real binding agent. If an antigen-antibody pair are chosen for the binding system of the affinity capacitor, the "dummy" antibody would be selected from the same class of antibodies and from the same type of animal, but would not be biospecific with the analyte antigen. The reference capacitor may use only the immobilized "dummy" analyte layer, and not the "dummy" binding layer. Alternatively, the reference capacitor may use the same antigen-antibody pair as the affinity capacitor but a molecular sieve would be used to prevent the analyte from entering the reference capacitor. Each of the different types of reference capacitors outlined above compensates for non-analyte changes in the fluid medium. However, a multiplicity of reference capacitors could be used with one affinity capacitor. These reference capacitors would identify the end points and/or other specific points of the dose-/response curve. The analyte concentration would be determined by the dielectric change in the analyte affinity capacitor as compared to the boundary values provided by the reference capacitors.

The molecular sieves enable the invented affinity sensor to be immersed in the test fluid. The molecular sieve provides two functions: (1) it retains the binding agent molecules in the sensor; and, (2) it selectively screens certain larger molecules from entering the "open" capacitor sensor. The molecular sieve is of a known construction having a pore size that can easily pass the fluid and analyte molecules but will not allow the larger binding agent molecules to escape from the sensor. The pore size for an antigen-antibody binding system would be less than 150,000 daltons to keep the antibody within the sensor. Molecular sieves are particularly useful when the sensor is an in vivo sensor implanted, for example, in a patient's blood stream. The molecular sieve prevents the binding agent molecules released by the binding system from being removed by the blood flow from the sensor. The following non-limiting examples, describe several specific embodiments of the differential sensor:

Example 1. Competitive binding embodiment. The analyte or analyte analog is immobilized on the passivation surface with linking molecules forming the first layer of the biochemical binding system. An analyte specific antibody is conjugated to the immobilized analyte species and forms the second layer of the biochemical binding system. The sensor is enclosed by a molecular sieve membrane with pores large enough to be permeable to the analyte but small enough to confine antibodies on or close to the sensor. This example is appropriate for small and medium molecular weight analytes compared to antibodies, which have molecular weights of approximately 150,000 daltons. With this example, the most appropriate, but not exclusive, reference capacitor is made exactly the same way as the analyte sensitive side, except that a "dummy" analyte and its associated specific "dummy" antibody is used. The "dummy" analyte and its specific antibody are chosen to have an affinity constant and other physical characteristics that closely match the analyte and analyte specific antibody characteristics. The reference capacitor is also enclosed by a molecular sieve. A second reference capacitor configuration with no bound "dummy" antibody may also be used.

Example 2. Direct Binding Embodiment. An antibody specific to particular cells, such as bacteria or to viruses, or to large molecules, is immobilized on the surface of the "open" capacitor by linking molecules, forming the binding agent molecules. A large molecule, bacterium, or virus, when bound to this antibody, will displace a significant amount of the fluid molecules, (predominantly water molecules) from the biological binding layer, and thus cause a detectable change in capacitance. In this case, a molecular sieve membrane would not be required. However, it would be useful to cover the surface with a mesh. The reference side of this sensor consists of a capacitor with a "dummy" antibody immobilized on the insulating substrate. This antibody is of the same class as the analyte sensitive antibody, but is made specific to a molecule not found in the test environment.

Example 3. Competitive Binding Equipment. This sensor is analogous to Example 1, but uses a receptor in place of an antibody as the second layer of the biochemical binding system. A generic sensor for neurotoxins can be configured using acetylcholine receptors. A substrate, such as succinylcholine, for which the receptor has affinity, is immobilized on the dielectric substrate, forming the first layer of the biochemical binding system. Receptor molecules are then conjugated to the substrate forming the second layer of the biochemical binding system. The receptor molecules are confined within the sensor by the use of a molecular sieve. When a neurotoxin permeates, the receptor is pulled off the surface, and capacitance changes. A reference capacitor is made identical to the analyte sensitive side except that the molecule chosen for surface immobilization is one with an affinity so large that substances of interest will not pull the receptor off the immobilized layer.

The above three examples show models that can be used for a large number of possible sensor configurations. It is to be understood that other binding agents and biochemical binding systems than those shown above are within the scope of this invention.

Binding Systems

As described earlier, for the direct binding embodiment, molecules of a binding agent are immobilized on the substrate surface with linking molecules; and, for the competitive binding configuration, a layer of the analyte or analyte-analog is immobilized on the substrate surface with linking molecules to form the first layer of the biochemical binding system. The attachment site on the molecule is chosen so that functional groups of the molecule have no interference. For example, in the direct binding embodiment, an antibody (the binding agent) is immobilized on the substrate so that its analyte recognizing and binding site or sites are free to function. For binding proteins, most reactions are nucleophilic with the nucleophilic group most often $NH_2$, OH or SH. Specific examples of biochemical binding systems are found in the art of affinity chromatography and are listed in Table II of Waters, R., "Affinity Chromatography", Analytical Chemistry, Volume 57, No. 11, pp. 1099A–1114A and listed in the figures on pages 19, 21 and 22 of Parikh, I., and P. Cuatrecasas, "Affinity Chromatography", Chemical and Engineering News, Aug. 26, 1985, pp. 17-32 these articles being incorporated here and by reference). Attachment reactions include the use of Cyanogen Bromide, Active Esters, Epoxide, Tresyl Chloride, Carbonyldiimidazole, Thiol and Diazonium reagents.

By way of illustration, the following experimental example performed by the Applicant shows covalent attachment of the biochemical binding system to the "open" affinity capacitor. The example is a sensor to detect the Trichothecene mycotoxin T-2, which is found in the environment and is produced by the fungal species Fuarium. Trichothecene mycotoxin is an agricultural toxin causing the loss of grain yield on various food crops. It has been implicated in human and animal mucotoxicoses.

Experimental Example

1. The "open" capacitor is coated with a 0.3 micron thick layer of SiO. Without care to prevent hydration of the surface (dry vacuum), the surface becomes composed of silanol groups:

$$\begin{array}{cc} OH & OH \\ | & | \\ Si\!\!-\!\!-\!\!-\!\!Si \end{array}$$

The surface will have approximately 10 silanols per $m_2$.

2. Amino groups are attached to the SiO surface for later attachment of proteins, using the following steps:
   a. soak substrate in 10% $\gamma$-aminopropyltriethoxysilane [$(EtO)_3$-Si-$(CH_2)_3$-$NH_2$] and dry toluene overnight at room temperature.
   b. wash with dry toluene; and,
   c. dry at 60 degrees C for two hours. The aminosilanized surface will be:

$$\text{Si}-\text{O}-\text{Si}-(\text{CH}_2)_3-\text{NH}_2$$

3. The surface is now ready for introduction of the Trichothecene (T-2) groups.
   a. The T-2 molecule is converted to a hemisuccinate derivative by heating it in the presence of Pyridine and Succinic anhydride. This derivization was necessary in this example, but some hemisuccinates can be bought off the shelf. For example, in making a hydrocortisone sensor, hydrocortisone hemisuccinate can be purchased directly from Sigma Chemical Co., and others.
   b. The hemisuccinate derivative of the analyte is then conjugated to the - amino function of the silanized surface, using a water soluble carbodiimide as a catalyst. The T-2 analyte is now immobilized on the surface of the "open" capacitor and the surface appears as follows:

$$\text{structure: T-2 derivative} - \text{OC}-\text{CH}_2\text{CH}_2\text{C}-\text{NH}-\text{CH}_2\text{CH}_2\text{CH}_2-\text{Si}-\text{O}-\text{Si}$$

4. The second layer of the biochemical binding system is produced by adding the anti T-2 toxin antibody to fluid bathing the surface of the open face capacitor. The antibodies will bind with an affinity similar to that in the standard immunoassay ($5.28 \times 10^7$ liters/mol). The resulting biochemical binding system has a first layer of the T-2 analyte immobilized on the surface and a second layer of the anti T-2 toxin antibody specifically bound to the immobilized layer.

Since the anti T-2 antibodies and the immobilized T-2 toxin are in dynamic equilibrium, an influx of free T-2 toxin molecules would perturb the equilibrium and draw the antibodies from the immobilized surface forming free analyte-antibody complexes. Removal of the free analyte-antibody complexes from the region of the capacitor sensor having higher field intensity, region $V_1$, causes a change in the capacitance that is a direct indication of the concentration of free T-2 molecules in the fluid medium.

Processing Circuit

Figure 6:
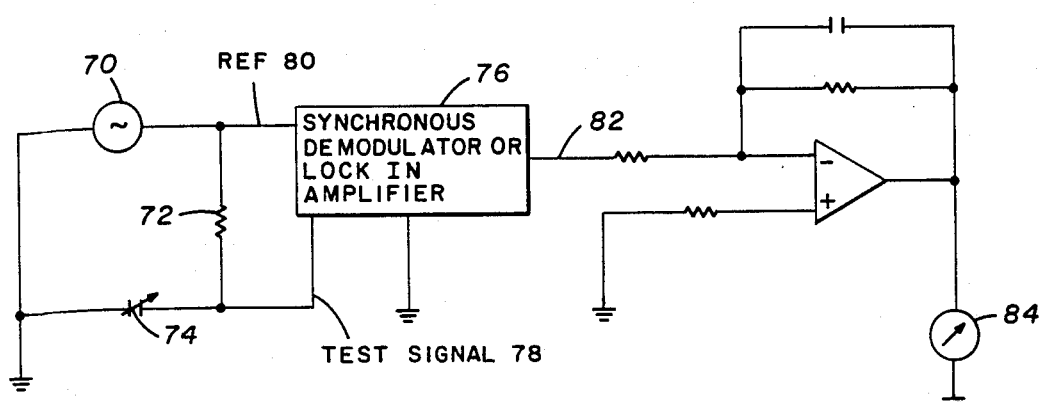
FIG. 6 is a schematic diagram of the processing circuitry used with the capacitive sensor.

FIG. 6 is a schematic drawing at a typical processing circuit for use with the capacitive affinity sensor. The heart of the system is a synchronous demodulator (also called a lock-in amplifier.) Applicant used a synchronous demodulator incorporated on an integrated circuit (IC NE5520 manufactured by Signetics Corp.). A sinusoidal voltage generator 70, generates a voltage provided to a circuit having a reference impedance 72, and the capacitance affinity sensor 74. The synchronous demodulator 76 produces an output determined by the phase of and amplitude of the input signal 78 with reference to the reference signal 80. The output 82 is amplified and a voltage readout 84 provides a signal indicative of the change of capacitance of affinity sensor 74.

Obviously many modifications and variations of the present invention are possible in light of the above teachings. It is therefore to be understood that within the scope of the appended claims the invention may be practiced otherwise than as specifically described.

What is claimed is:

1. A device for detecting the presence of an analyte in a fluid having an aqueous solvent, said device comprising:
   a sensing capacitor including:
      a substrate having a first conductor and a second conductor spaced a distance from said first conductor,
      an electrically insulating layer covering said first and second conductors, said electrically insulating layer defining a surface,
      a binding agent selected from the group consisting of antigens, haptens, bioreceptors and antibodies capable of biospecifically binding with the analyte,
      a linking molecule adapted for and covalently bonding said binding agent to said surface and extending said binding agent a distance from said surface to minimize steric hindrance between the analyte and the surface; and,
   a circuit means, electrically coupled to said sensing capacitor, responsive to changes in capacitance between said first and second conductors.

2. The device of claim 1, wherein said linking molecule extends said binding agent out beyond the electrical double layer.

3. A device for detecting the present of an analyte in a fluid having an aqueous solvent, said device comprising:
   a sensing capacitor including:
      a substrate having a first conductor and a second conductor spaced a distance from said first conductor,
      a binding agent selected from the group consisting of antigens, adapters, bioreceptors and antibodies capable of biospecifically binding with the analyte,
      an electrically insulating layer covering said first and second conductors, said electrically insulating layer defining a surface, wherein the composition and thickness of said insulating layer is selected to produce a series capacitance smaller than the double layer series capacitance and approaching the series capacitance produced by the binding agent, a linking molecule adapted for and covalently bonding said binding agent to said surface; and, a circuit means, electrically coupled to said sensing capacitor, responsive to changes in capacitance between said first and second conductors.

4. The device of claim 3, wherein the thickness and composition of said insulating layer is selected to produce a series capacitance less than 1 $\mu f/cm^2$.

5. The device of claim 3, wherein said insulating layer comprises an inner thin film of high dielectric ion impervious material and an outer layer of a material selected to provide binding compatbility with said linking molecules.

6. The device of claim 5, wherein said inner thin film is composed of silicon nitride and said outer layer is composed of silica ($SiO_2$).

7. The device of claim 1, wherein said first conductor comprises a plurality of fingers disposed on said substrate and wherein said second conductor comprises a plurality of fingers disposed on said substrate, fingers of said first conductor are interdigitated with fingers of said second conductor.

8. The device for detecting the presence of an analyte in a liquid, said device comprising:
a sensing capacitor including,
a substrate having a first conductor and a second conductor spaced a distance from said first conductor,
an electrically insulating layer covering said first and second conductors, said electrically insulating layer defining a surface,
a first organic compound having a biospecific binding site,
a linking molecule adapted for and covalently bonding said first organic compound to said surface, and extending said first organic compound a distance from said surface to minimize steric hinderance between the analyte and the surface,
a binding agent composed essentially of an organic compound selected from the group consisting of antibodies, lectins, enzymes, and neural receptors and being reversibly bound to said first organic compound, said binding agent biospecifically reactive with both said first organic compound and said analyte, wherein exposure of said binding agent to a liquid containing analyte causes formation of a binding agent/analyte complex through competitive binding, said binding agent/analyte complex being free to diffuse from said surface; and,
a circuit means, electrically coupled to said sensing capacitor, responsive to changes in capacitance between said first and second conductors.

9. The device of claim 8, wherein said linking molecule extends said first organic component out beyond the electrical double layer.

10. A device for detecting the presence of an analyte in a liquid, said device comprising:
a sensing capacitor including,
a substate having a first conductor and a second conductor spaced a distance from said first conductor,
an electrically insulating layer covering said first and second conductors, said electrically insulating layer defining a surface, wherein the composition and thickness of said insulating layer is selected to produce a series capacitance smaller than the double layer series capacitance,
a first organic compound having a biospecific binding site,
a linking molecule adapted for and covalently bonding said first organic compound to said surface,
a binding agent composed essentially of an organic compound selected from the group consisting of antibodies, lectins, enzymes, and neural receptors and neural receptors and being reversibly bound to said first organic compound, said binding agent biospecifically reactive with both said first organic compound and said analyte, wherein exposure of said binding agent to a liquid containing analyte causes formation of a binding agent/analyte complex through competitive binding, said binding agent/analyte complex being free to diffuse from said surface; and,
a circuit means, electrically coupled to said sensing capacitor, responsive to changes in capacitance between said first and second conductors.

11. The device of claim 10, wherein the thickness and composition of said insulating layer is selected to produce a series capacitance less than 1 $\mu f/cm^2$.

12. The device of claim 10, wherein said insulating layer comprises an inner thin film of high dielectric ion impervious material and an outer layer of a material selected to provide binding compatibility with said linking molecules.

13. The device of claim 12, wherein said inner thin film is composed of silicon nitride and said outer layer is composed of silica ($SiO_2$).

14. The device of claim 8, wherein said first conductor comprises a plurality of fingers disposed on said substrate and wherein said second conductor comprises a plurality of fingers disposed on said substrate, fingers of said first conductor are interdigitated with fingers of said second conductor.

15. The device of claim 8, further comprising a membrane encompassing said first and second conductors, said membrane having a pore size selected to pass analyte but not to pass said binding agent, so that said binding agent is retained in a volume adjacent to said first and said conductor encompassed by said membrane.

16. The device of claim 8, further comprising:
a reference capacitor comprising a substrate having a first conductor spaced apart from a second conductor, an electrically insulating layer covering such first and second conductor, said electrically insulating layer defining a reference surface; and,
a reference circuit, electrically coupled to a said reference capacitor, responsive to changes in capacitance between said first and second conductors.

* * * * *